(12) United States Patent
Fry et al.

(10) Patent No.: US 6,685,640 B1
(45) Date of Patent: Feb. 3, 2004

(54) ABLATION SYSTEM

(75) Inventors: Francis J. Fry, Port Charlotte, FL (US); Michael H. Phillips, Indianapolis, IN (US); Narendra T. Sanghvi, Indianapolis, IN (US)

(73) Assignee: Focus Surgery, Inc., Indianapolis, IN (US)

( * ) Notice: Subject to any disclaimer, the term of this patent is extended or adjusted under 35 U.S.C. 154(b) by 0 days.

(21) Appl. No.: 09/647,317

(22) PCT Filed: Mar. 30, 1999

(86) PCT No.: PCT/US99/06974

§ 371 (c)(1),
(2), (4) Date: Sep. 28, 2000

(87) PCT Pub. No.: WO99/49788

PCT Pub. Date: Oct. 7, 1999

Related U.S. Application Data

(60) Provisional application No. 60/079,945, filed on Mar. 30, 1998.

(51) Int. Cl.$^7$ .................................................. A61B 8/14
(52) U.S. Cl. ...................... 600/439; 600/437; 600/606; 600/27
(58) Field of Search ..................... 128/660; 607/97; 606/27; 600/440, 439, 437; 601/2, 328

(56) References Cited

U.S. PATENT DOCUMENTS

| | | | |
|---|---|---|---|
| 4,620,546 A | 11/1986 | Aida et al. | |
| 4,658,828 A | 4/1987 | Dory | |
| 4,858,613 A | 8/1989 | Fry et al. | |
| 4,951,653 A | 8/1990 | Fry et al. | |
| 4,955,365 A | 9/1990 | Fry et al. | |
| 5,036,855 A | 8/1991 | Fry et al. | |
| 5,054,470 A | 10/1991 | Fry et al. | |
| 5,080,102 A | * 1/1992 | Dory | 128/660 |
| 5,117,832 A | 6/1992 | Sanghvi et al. | |
| 5,215,680 A | 6/1993 | D'Arrigo | |
| 5,219,401 A | 6/1993 | Cathignol et al. | |
| 5,247,935 A | 9/1993 | Cline et al. | |
| 5,295,484 A | * 3/1994 | Marcus et al. | 128/660 |
| 5,330,518 A | 7/1994 | Neilson et al. | |
| 5,409,006 A | 4/1995 | Buchholtz et al. | |
| 5,443,069 A | 8/1995 | Schaetzle | |
| 5,480,417 A | 1/1996 | Hascoet et al. | |
| 5,620,479 A | * 4/1997 | Diederich | 607/97 |
| 5,630,837 A | * 5/1997 | Crowley | 601/2 |
| 5,666,954 A | 9/1997 | Chapelon et al. | |
| 5,676,692 A | * 10/1997 | Sanghvi et al. | 607/97 |
| 5,840,031 A | * 11/1998 | Crowley | 600/440 |
| 5,895,356 A | 4/1999 | Andrus et al. | |
| 2002/0022833 A1 | * 2/2002 | Maquire et al. | 606/27 |

* cited by examiner

*Primary Examiner*—Henry Bennett
*Assistant Examiner*—Sabrina Dagostino
(74) *Attorney, Agent, or Firm*—Barnes & Thornburg

(57) ABSTRACT

An apparatus for ablating tissue within a treatment region includes an ultrasound treatment transducer (36, 36') for orienting at a first longitudinal orientation and a first angular orientation (40, 42) within the treatment region (26), for orienting at the first longitudinal orientation and a second angular orientation (40, 42) within the treatment region, and for orienting at a second longitudinal orientation and the first angular orientation (40, 42) within the treatment region, and a drive system for exciting (via conductors 46) the transducer (36, 36') to ablate tissue (60) oriented adjacent the first longitudinal orientation and the first angular orientation within the treatment region (26), adjacent the first longitudinal orientation and the second angular orientation within the treatment region (26), and adjacent the second longitudinal orientation and the first angular orientation within the treatment region (26), respectively.

12 Claims, 2 Drawing Sheets

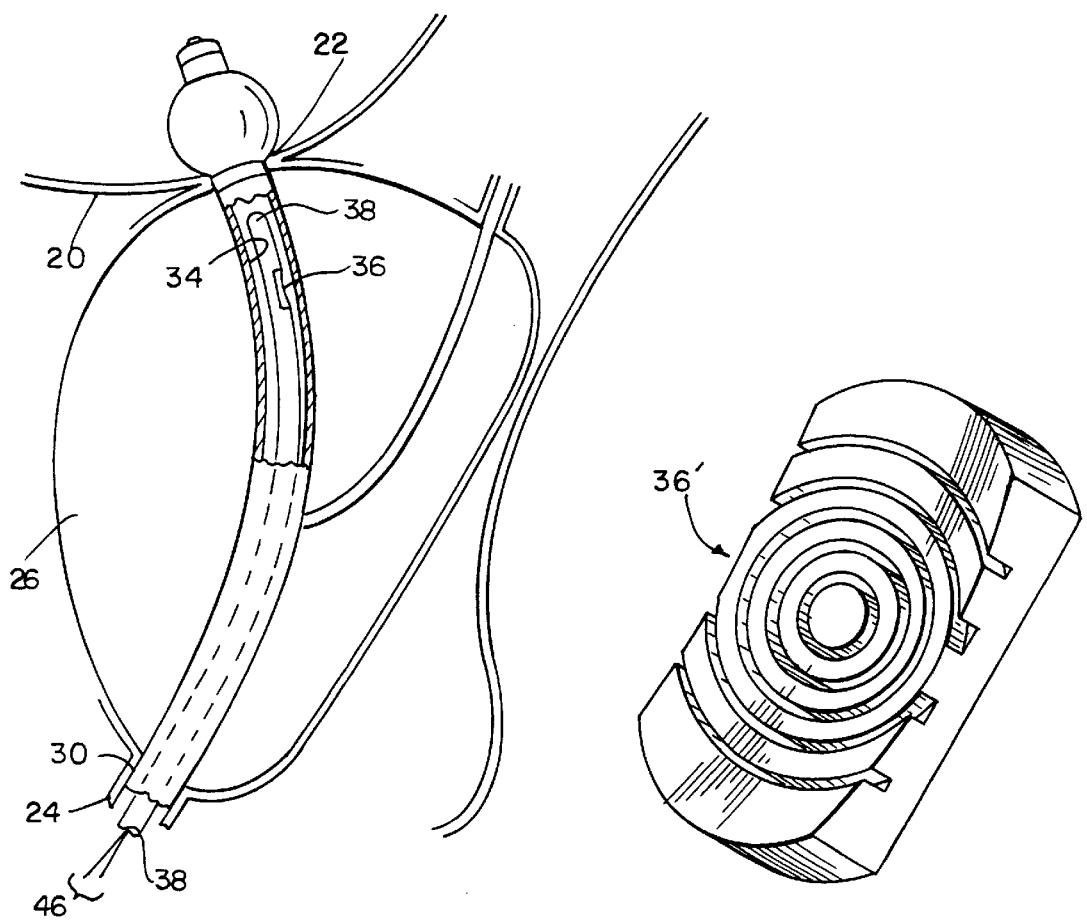
FIG. 1
FIG. 3
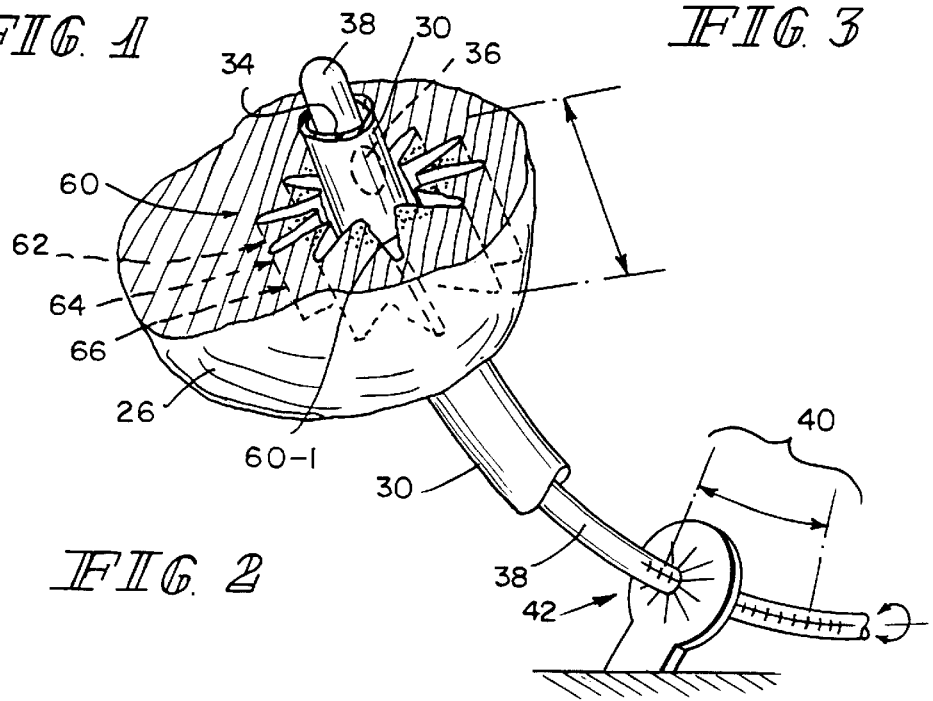
FIG. 2

ABLATION SYSTEM

CROSS-REFERENCE TO RELATED APPLICATIONS

This application is a U.S. national application of international application serial No. PCT/US99/06974 filed Mar. 30, 1999, which claims priority to U.S. provisional application serial No. 60/079,945 filed Mar. 30, 1998.

BACKGROUND OF THE INVENTION

This invention relates to techniques and apparatus for achieving ablation of tissue through the use of focussed ultrasound. It is disclosed in the context of a system and method for the ablation of prostate tissue in the treatment of, for example, benign prostate hyperplasia (BPH), but is believed to be applicable to the treatment of other conditions as well.

The use of transrectally applied high intensity focussed ultrasound in the treatment of diseases of the prostate is well documented. There are, for example, the disclosures of U.S. Pat. Nos. 5,117,832 and 5,676,692 and Fry, F. J. et al, "Ultrasound and Microbubbles: Their Generation, Detection and Potential Utilization in Tissue and Organ Therapy—Experimental," Ultrasound in Med. and Biol., vol. 21, no. 9, pp. 1227–1237, 1995 and Sanghvi, N. T., et al, "Noninvasive Surgery of Prostate Tissue by High-Intensity Focused Ultrasound," IEEE Transactions on Ultrasonics, Ferroelectrics, and Frequency Control, vol. 43, no. 6, pp. 1099–1110, November 1996. U.S. Pat. Nos. 5,409,006 and 5,443,069 also disclose the application of ultrasound for the treatment of BPH. Several references disclose the treatment of BPH by electromagnetic radiation, for example, microwaves, applied transrectally, transurethrally or otherwise. Illustrative of these references are U.S. Pat. Nos.: 5,330,518 and 5,480,417. Other ultrasound applications for the treatment of disease are illustrated in, for example, U.S. Pat. Nos. 5,247,935; 5,219,401; 5,215,680; 5,149,319; 5,054,470; 5,036,855; 4,955,365; 4,951,653; 4,858,613; 4,658,828; 4,586,512; and, 4,620,546. The disclosures of these references are incorporated herein by reference.

Although the prostate can effectively be treated transrectally, urologists are trained in the transurethral treatment of the prostate. As a result, there has been some resistance to transrectal treatment of the prostate. The present invention is disclosed in the context of transurethral treatment of the prostate.

DISCLOSURE OF THE INVENTION

According to one aspect of the invention, a method for treating tissue includes orienting an ultrasound transducer at a first longitudinal orientation and a first angular orientation adjacent a treatment region, exciting the transducer to ablate tissue adjacent the first longitudinal orientation and the first angular orientation within the treatment region, orienting the transducer at the first longitudinal orientation and a second angular orientation adjacent the treatment region, exciting the transducer to ablate tissue adjacent the first longitudinal orientation and the second angular orientation within the treatment region, orienting the transducer at a second longitudinal orientation and the first angular orientation adjacent the treatment region, and exciting the transducer to ablate tissue adjacent the second longitudinal orientation and the first angular orientation within the treatment region.

According to another aspect of the invention, a method of treating tissue comprises orienting an ultrasound transducer at a first longitudinal orientation and a first angular orientation adjacent the treatment region, exciting the transducer to ablate tissue adjacent the first longitudinal orientation and the first angular orientation within the treatment region, orienting the transducer at a second longitudinal orientation and a second angular orientation adjacent the treatment region, and exciting the transducer to ablate tissue adjacent the second longitudinal orientation and the second angular orientation within the treatment region.

Illustratively according to these aspects of the invention, orienting the transducer at a first longitudinal orientation and a first angular orientation includes positioning a catheter including a lumen adjacent the treatment region, maintaining substantially the position of the catheter adjacent the treatment region, and passing the transducer into the lumen so that the transducer is oriented adjacent the treatment region.

Further illustratively according to these aspects of the invention, the method includes providing an indicator for indicating the longitudinal and angular orientation of the transducer.

Further illustratively according to these aspects of the invention, the method includes providing a drive system for driving the transducer, providing the transducer and providing the drive system together including providing an ultrasound transducer and drive system having a variable focal length.

Additionally illustratively according to these aspects of the invention, positioning a catheter adjacent the treatment region includes positioning a catheter including a balloon region adjacent the treatment region and filling the balloon region to maintain substantially the position of the catheter adjacent the treatment region.

According to another aspect of the invention, an apparatus for treating tissue includes an ultrasound transducer for orienting at a first longitudinal orientation and a first angular orientation adjacent a treatment region, for orienting at the first longitudinal orientation and a second angular orientation adjacent the treatment region, and for orienting at a second longitudinal orientation and the first angular orientation adjacent the treatment region, and a drive system for exciting the transducer to ablate tissue adjacent the first longitudinal orientation and the first angular orientation within the treatment region, adjacent the first longitudinal orientation and the second angular orientation within the treatment region, and adjacent the second longitudinal orientation and the first angular orientation within the treatment region, respectively.

According to another aspect of the invention, an apparatus for treating tissue includes an ultrasound transducer for orienting at a first longitudinal orientation and a first angular orientation adjacent a treatment region, and for orienting at a second longitudinal orientation and a second angular orientation adjacent the treatment region, and a drive system for exciting the transducer to ablate tissue adjacent the first longitudinal orientation and the first angular orientation within the treatment region, and adjacent the second longitudinal orientation and the second angular orientation within the treatment region.

Illustratively according to these aspects of the invention, the apparatus further includes a catheter including a lumen for positioning adjacent the treatment region, the lumen permitting passage of the transducer into the lumen so that the transducer can be oriented adjacent the treatment region.

Further illustratively according to these aspects of the invention, the apparatus includes an indicator for indicating the longitudinal and angular orientation of the transducer.

Additionally illustratively according to these aspects of the invention, the transducer and the drive system together include a transducer and drive system having a variable focal length.

Illustratively according to these aspects of the invention, the catheter includes a balloon region adjacent the treatment region, filling the balloon region maintaining substantially the position of the catheter.

BRIEF DESCRIPTION OF THE DRAWINGS

The invention may best be understood by referring to the following detailed description of an illustrative embodiment of the invention and the accompanying drawings. In the drawings:

FIG. 1 illustrates a fragmentary sectional side elevational view of an apparatus constructed according to the invention in place in the urethra and bladder of a patient being treated for BPH;

FIG. 2 illustrates a fragmentary perspective view taken generally along section lines 2—2 of FIG. 1;

FIG. 3 illustrates a transducer useful in performing methods according to the invention;

DETAILED DESCRIPTIONS OF ILLUSTRATIVE EMBODIMENTS

Figure 4:
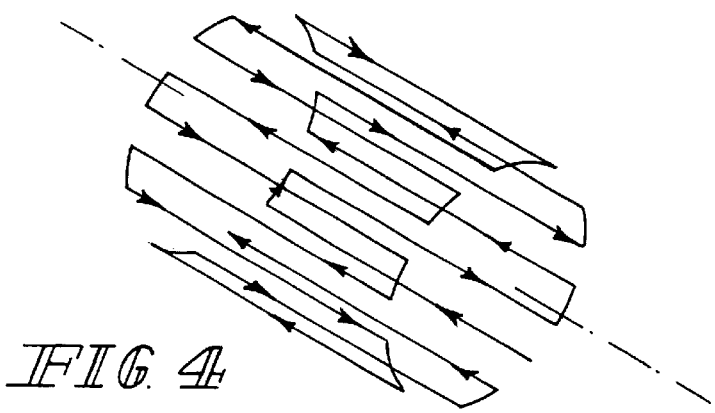
FIG. 4 illustrates another treatment method which will produce a treatment lesion similar to the one illustrated in FIG. 2; and, FIG. 5 illustrates a fragmentary sectional side elevational view of another apparatus constructed according to the invention.

FIG. 1 illustrates the lower portion of the bladder 20, bladder neck 22 and the upper portion of the urethra 24 of a patient suffering from BPH. The prostate 26 which surrounds the upper portion of the urethra directly beneath the bladder 20 and around the bladder neck 22 becomes enlarged. The symptoms of the disease are well known and discomforting. They generally result from the obstruction of the urethra by the enlarged prostate tissue. If not treated effectively, the disease can become complicated with devastating effect. The classical surgical treatment is resection of some portion of the prostate transurethrally. While this method of treatment is frequently effective in the treatment of BPH, it is sometimes contraindicated by, for example, the patient's condition, reluctance of the patient based upon potential side effects, and so on.

According to the invention, a transurethral catheter 30 having a balloon end region 32 to aid in positioning the catheter 30 relative to the prostate 26 includes a lumen 34 in which is oriented a small ultrasound transducer 36 mounted on a support 38, such as a stiff wire. Support 38 permits manipulation of the transducer 36 into the orientations necessary and/or desirable to treat the prostate 36 in the manner which will be outlined hereinafter. At the same time however, some mechanism must be provided for satisfying the treating physician that the transducer 36 is properly oriented in the urethra 24 and prostate 26 prior to a given step in the treatment. This may mean providing some sort of index or indicator 40 on the support 38 or on the transducer 36 which may be used in conjunction with some sort of visualization scheme, such as, for example, a transrectal ultrasound visualization system, and/or making the support 38 sufficiently torque-resistant and providing an indicator 42 on the outer end 44 of catheter 30 so that the treating physician can determine the orientation of the transducer 36.

Transducer 36 itself may be excited in a visualization mode in accordance with known techniques to aid in the process of orienting transducer 36 appropriately for the high intensity focussed ultrasound treatment that is to follow.

In any event, once the treating physician is satisfied of the positioning of the transducer 36, the transducer 36 is excited through appropriate electrical conductors 46 which extend through the lumen 34 from an ultrasound frequency generator 48. Relatively high energy density ultrasound, high enough that, once focussed by the transducer 36, it can either cause cavitation-induced injury and, ultimately, necrosis or elevate the temperature of the tissue sufficiently high, for example, 43° C., for a sufficient time to cause necrosis, is transmitted by the transducer 36 into the tissue of the prostate 26, setting in motion the mechanisms of necrosis in the region of the transducer 36's focal point 52 and in the near field between the transducer 36 and the focal region in prostate 26. After necrosis begins, the necrotized tissue is resorbed into the body, relieving the symptoms of BPH experienced by the patient. The generator 48 must be capable of exciting the transducer 36 in the treatment mode with energies high enough to induce hyperthermia at the focal region when the transducer 36 is operated in the treatment mode. Energies in the range of hundreds of volts peak for times in the range of milliseconds ordinarily will achieve cavitation-induced necrosis in the focal zone. In the near field between the transducer 36 and the focal zone, lower exciting energies for longer periods of time, in the range of, for example, four to twenty seconds or so, provide hyperthermia-induced necrosis. Thus, different ultrasound-related phenomena can be employed by the treating physician to achieve tissue necrosis. Resorption will typically follow in due course.

Using a transducer 36 which has a relatively short focal length increases the likelihood that all of the treated tissue can be constrained to the prostate. A transducer 36' (FIG. 3) with a variable focal depth, such as one of the general type illustrated in U.S. Pat. No. 4,586,512, and supplied with ultrasound exciting signals related to each other as outlined in that patent, can be used to advantage to vary the focus of such a transducer 36' in such a treatment scheme. For example, the proper focal depth to treat any given depth of the prostate from the transducer's location in the urethra can be selected and the transducer 36' excited accordingly. Alternatively, or perhaps additionally, an appropriate frequency of excitation to provide the desired depth of ultrasound penetration and tissue treatment can be selected for any given treatment depth. The treatment time can be established in accordance with known principles and guidelines. Guidelines can also be established for target, or desired, treatment lesion size and shape. One example of the flexibility of this method in the treatment of BPH can be appreciated by referring to FIG. 2.

In FIG. 2, the diseased prostate 26 is illustrated in perspective, and is sectioned at about the level at which the transducer 36 resides in the urethra 24. After treatment of the prostate 26 with the transducer 36 oriented at a specific angle of, for example, 0°, corresponding to vertically upward in FIG. 2, a radially extending, or ray, lesion 60-1 is formed. The tissue in this lesion begins to necrose. The transducer support 38 is manipulated to turn transducer 36 so that its focal point now lies on a ray or radius extending at an angle of, for example, 5° clockwise from vertical in FIG. 2. Another treatment step just like the first is conducted, resulting in a second ray lesion 60-2. The tissue in this lesion begins to necrose. This process continues until a somewhat star- or bicycle wheel spokes-shaped composite lesion 60 is formed. The support is then manipulated to move the transducer's focal point into a plane adjacent, but spaced slightly from, the plane of lesion 60. The entire process is repeated, forming an adjacent and desirably overlapping star- or bicycle wheel spokes-shaped lesion 62. The treating physician proceeds along the urethra in this manner, forming a number of adjacent and desirably overlapping lesions 60, 62, 64, 66, . . . . Necrosis of BPH tissue adjacent the urethra 24 results, eventually relieving the patient's symptoms.

Of course, the treating physician can also proceed along the length of the urethra 24 in the treatment zone first, and then reorient the transducer 36 angularly and move the transducer 36 along a path adjacent to the path followed during formation of the first lesion, repeating this process until a desired number of adjacent spoke-like lesions extending along the length of the desired treatment zone are formed. Such a path is illustrated in FIG. 4. Other procedures can also be followed to produce a composite lesion such as the one illustrated in FIG. 2, or any other desired configuration of lesion.

Figure 5:
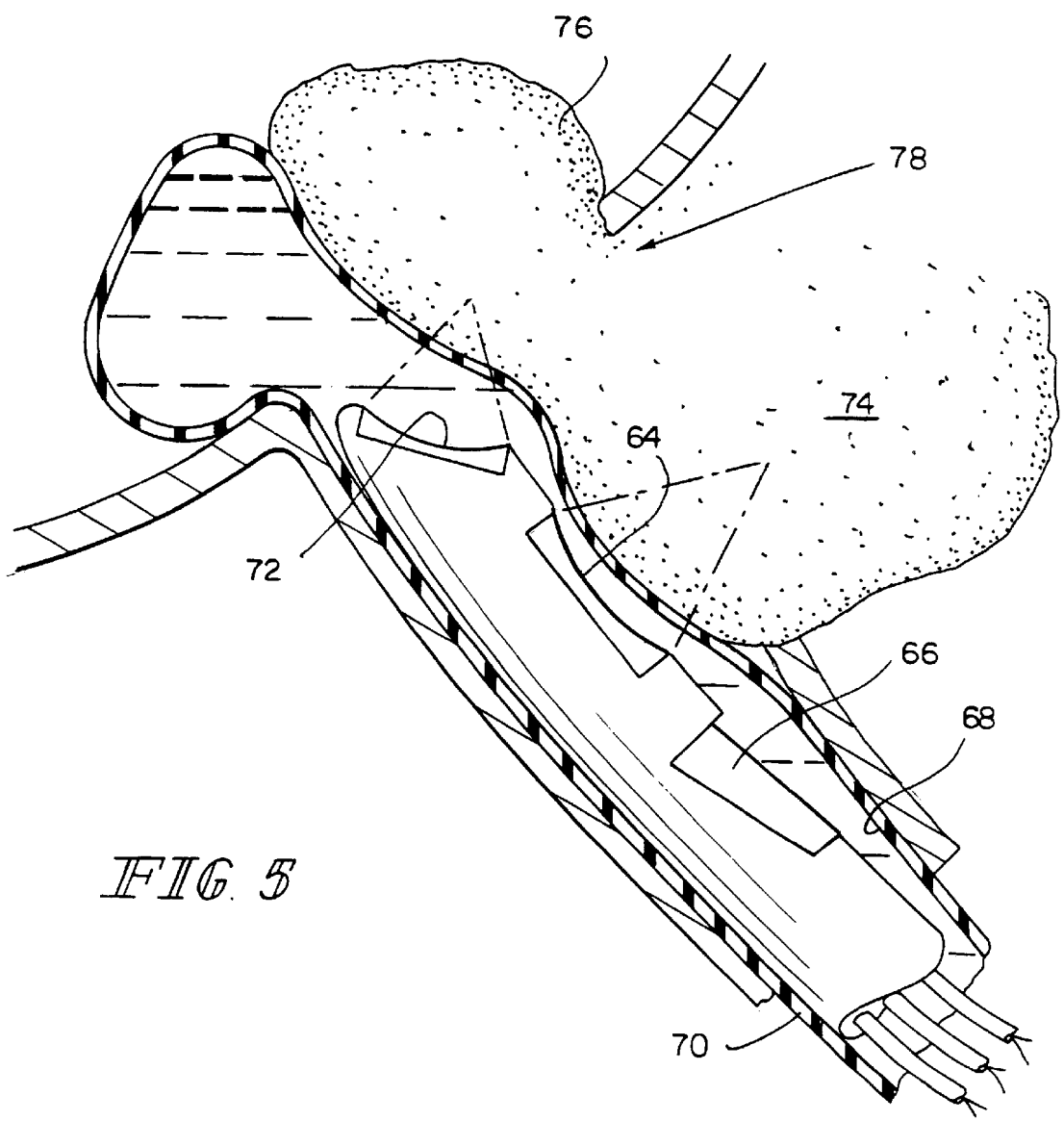

The transducer 36 can be a composite type, as illustrated by transducer 36' in FIG. 3. Other multi-element transducer types, such as two or more single element transducers side by side in lumen 34, can be employed with one element operated in a visualization mode and one in a treatment mode. One such composite transducer is illustrated in FIG. 5. This composite transducer puts a treatment transducer 64 and a visualization transducer 66 side by side in the lumen 68 of a catheter 70. Additionally, this composite transducer adds another treatment transducer 72 which can be excited separately from treatment transducer 64 and/or visualization transducer 66. While the treatment transducers 36, 64 will effectively treat the main lobes of the prostate 74, a median lobe 76 of the prostate 74 of a BPH sufferer can grow inside the bladder neck 78. This median lobe can be difficult to treat using transducers oriented as transducers 36, 64 are. The transducer 72 oriented to face toward the remote end 74 of catheter 70 and at an angle α, 0°<α<90° to the longitudinal extent of catheter 70, permits treatment of the median lobe 76 of the prostate 74 to relieve the symptoms of BPH caused by enlargement of the median lobe 76 into the bladder neck 78.

What is claimed is:

1. Apparatus for treating tissue including an ultrasound transducer for orienting at a first longitudinal orientation and a first angular orientation adjacent the treatment region, at a second longitudinal orientation and the first angular orientation adjacent the treatment region, and at the first longitudinal orientation and a second angular orientation adjacent the treatment region, a drive system for exciting the transducer to ablate tissue oriented adjacent the first longitudinal orientation and the first angular orientation within the treatment region, adjacent the second longitudinal orientation and the first angular orientation within the treatment region, and adjacent the first longitudinal orientation and the second angular orientation within the treatment region, respectively, and an indicator for indicating the longitudinal and angular orientation of the transducer adjacent the treatment region.

2. The apparatus of claim 1 further including a catheter including a lumen for positioning adjacent the treatment region, the lumen permitting passage of the transducer into the lumen so that the transducer can be oriented adjacent the treatment region.

3. The apparatus of claim 1 wherein the transducer and the drive system together include a transducer and drive system having a variable focal length.

4. The apparatus of claim 2 wherein the transducer and the drive system together include a transducer and drive system having a variable focal length.

5. The apparatus of claim 2 wherein the catheter includes a balloon region adjacent the treatment region, filling the balloon region maintaining substantially the position of the catheter.

6. The apparatus of claim 5 wherein the transducer and the drive system together include a transducer and drive system having a variable focal length.

7. Apparatus for treating tissue including an ultrasound transducer for orienting at a first longitudinal orientation and a first angular orientation adjacent the treatment region, and at a second longitudinal orientation and a second angular orientation adjacent the treatment region, and a drive system for exciting the transducer to ablate tissue oriented adjacent the first longitudinal orientation and the first angular orientation within the treatment region, and adjacent the second longitudinal orientation and the second angular orientation within the treatment region, respectively, and an indicator for indicating the longitudinal and angular orientation of the transducer adjacent the treatment region.

8. The apparatus of claim 7 including a catheter including a lumen for positioning adjacent the treatment region, the lumen permitting passage of the transduce into the lumen so that the transducer can be oriented adjacent the treatment region.

9. The apparatus of claim 8 wherein the catheter includes a balloon region adjacent the treatment region, filling the balloon region maintaining substantially the position of the catheter.

10. The apparatus of claim 8 wherein the transducer and the drive system together include a transducer and drive system having a variable focal length.

11. The apparatus of claim 7 wherein the transducer and the drive system together include a transducer and drive system having a variable focal length.

12. The apparatus of claim 9 wherein the transducer and the drive system together include a transducer and drive system having a variable focal length.

* * * * *